United States Patent [19]

Ferguson et al.

[11] Patent Number: 5,308,317
[45] Date of Patent: May 3, 1994

[54] PROTECTIVE TUBE LASER ENDOSCOPY

[75] Inventors: Mark K. Ferguson, Hinsdale; David Schucart, Highland Park; Lev Melinyshyn, Mt. Prospect, all of Ill.

[73] Assignee: Arch Development Corporation, Chicago, Ill.

[21] Appl. No.: 534,758

[22] Filed: Jun. 7, 1990

[51] Int. Cl.$^5$ .................................................. A61M 5/00
[52] U.S. Cl. ........................................ 604/22; 604/96; 604/101; 606/16
[58] Field of Search ............ 604/395, 397, 398, 207.15; 128/7, 13–16; 606/96, 99, 101–104, 22

[56] References Cited

U.S. PATENT DOCUMENTS

| | | | |
|---|---|---|---|
| 4,418,688 | 12/1983 | Loeb | 128/398 |
| 4,419,095 | 12/1983 | Nebergall et al. | 128/207.15 |
| 4,445,892 | 5/1984 | Hussein et al. | 606/15 |
| 4,475,548 | 10/1984 | Muto | 606/167 |

*Primary Examiner*—David M. Shay
*Attorney, Agent, or Firm*—Laff, Whitesel, Conte & Saret

[57] ABSTRACT

A protective tube for a laser endoscope that prevents the passage of laser smoke towards the oral cavity of a patient, removes debris from the endoscope and which is adapted to be inserted through the oral cavity and into an esophagus of a patient receiving medical treatment, the protective tube comprising a curved resilient member having a proximal end and a distal end, the proximal end including a mouthpiece and the distal end including a first sealing means and a second sealing means, the first sealing means forming a first seal between an outer surface of the tube and an inner surface of the esophagus and the second sealing means forming a second seal between an inner surface of the tube and an outer surface of the laser endoscope.

6 Claims, 3 Drawing Sheets

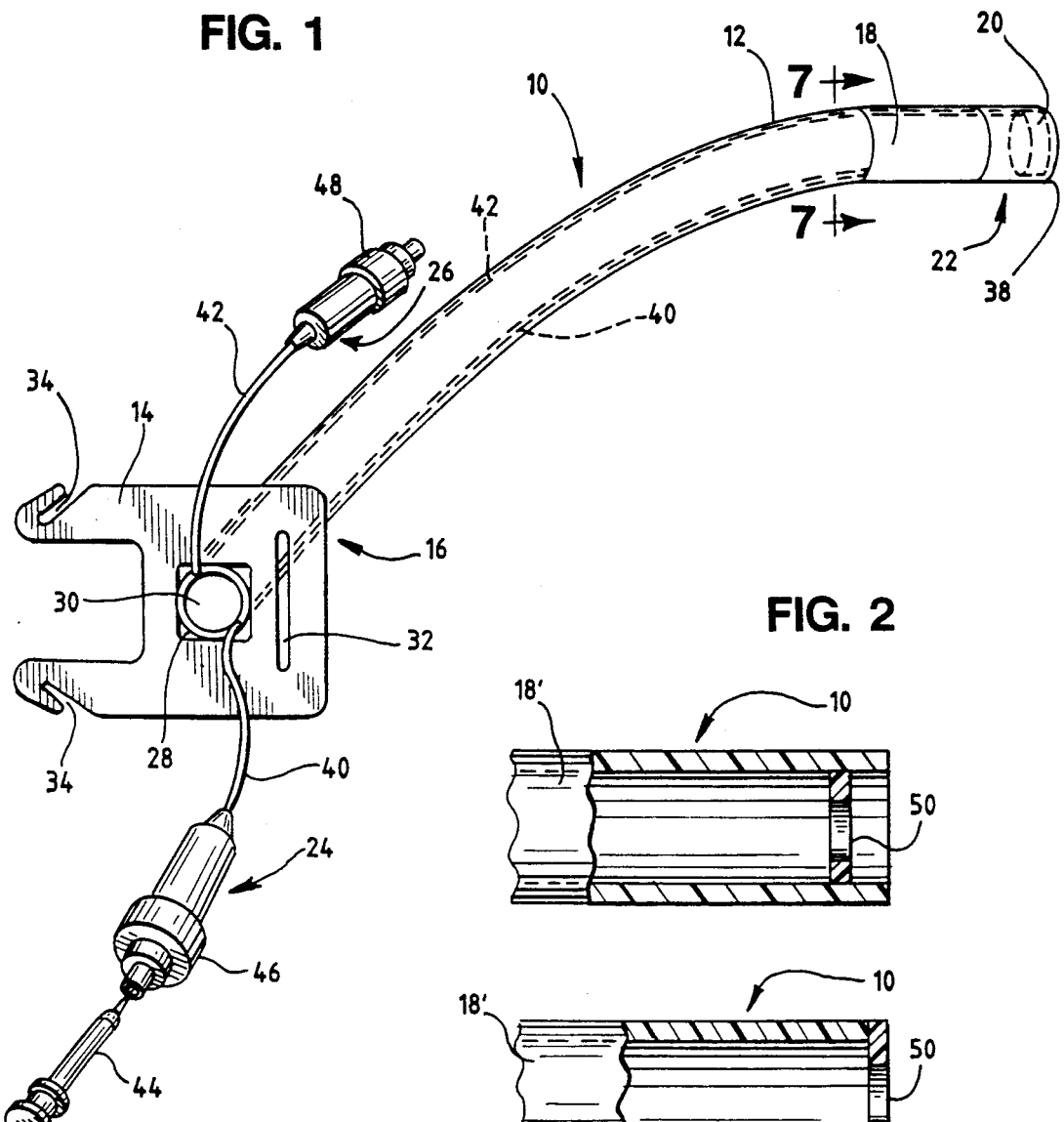
FIG. 1
FIG. 2
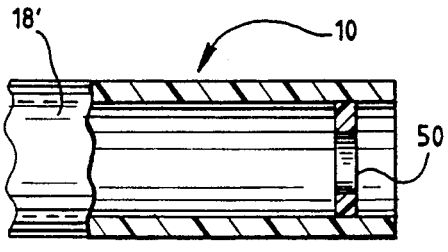
FIG. 2A
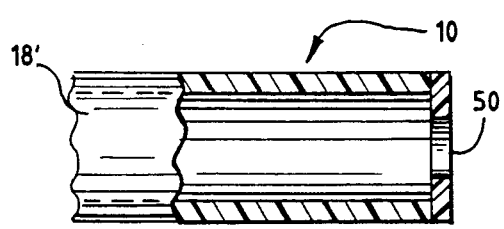
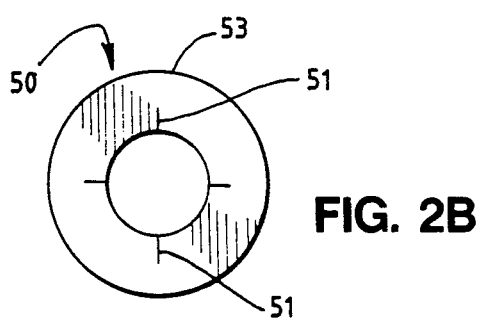
FIG. 2B

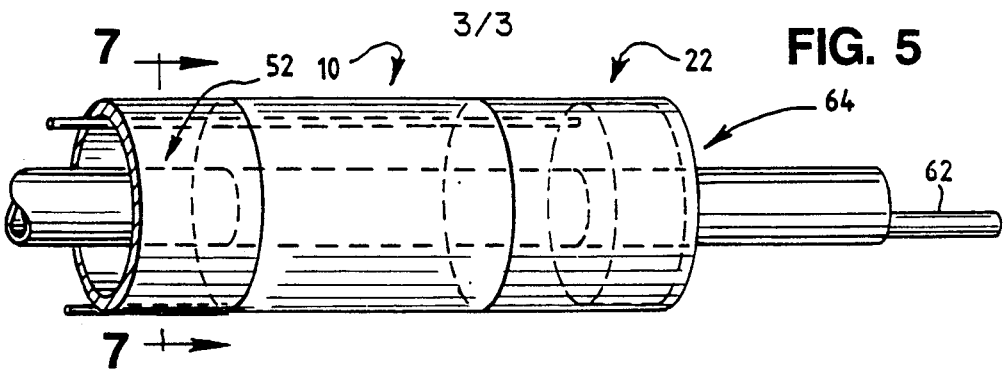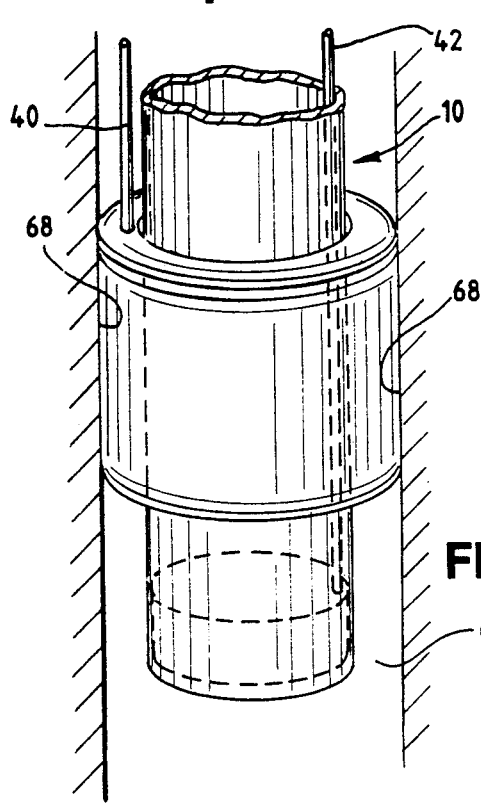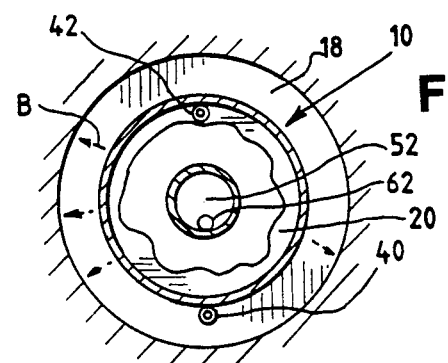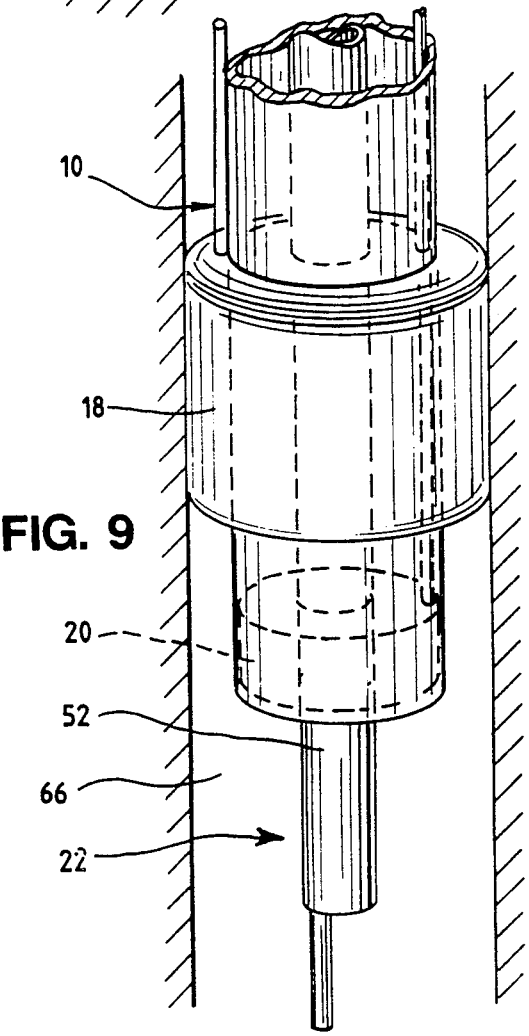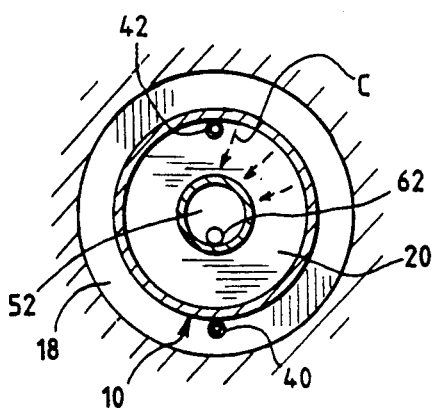

PROTECTIVE TUBE LASER ENDOSCOPY

FIELD OF THE INVENTION

This invention relates to a protective tube used for an endoscopic laser procedure. More particularly, this invention relates to a protective tube for an endoscopic laser procedure which prevents the passage of laser smoke towards the oral cavity of a patient, removes debris build-up from the laser and is adapted to be inserted through the oral cavity and into an esophagus of a patient receiving medical treatment.

BACKGROUND OF THE INVENTION

It is a common practice to perform both diagnostic and therapeutic esophageal endoscopy on human medical patients to discover and rectify abnormalities that may occur in the esophagus and portions of the stomach and duodenum. For example, endoscopy is frequently used in patients suspected of having reflux esophagitis, benign strictures, gastrointestinal distress and bleeding, esophageal rings, esophageal ulcers, malignant tumors and cancers. The aforementioned abnormalities may be treated by various techniques, including laser therapy. This is especially beneficial, among other things, in tumor removal, coagulation of ulcer beds and treatment of certain esophageal cancers. However, along with the many benefits of laser therapy, there are certain disadvantages, including the production of laser smoke which migrates towards the oral cavity, nasal passage and lungs and is injurious to these tissues. Specifically, the smoke causes oxygen depletion in the lungs and may contain viable cancer tissues which can affect the patient and operating room personnel. Another disadvantage of laser therapy is that debris produced from the laser often collects on the distal end of the endoscope. During removal of the endoscope from the patient, this same debris may adhere to any tissue or equipment it contacts, and may adhere to the endoscope during its reinsertion into the patient.

Despite the above-mentioned disadvantages, laser therapy is still widely used in conjunction with a variety of medical devices such as endoscopes, angioscopes, catheters and the like. For example, U.S. Pat. No. 4,770,653 discloses a catheter for laser angioplasty that includes a positioning means in the form of an expandable balloon at its distal end. Expansion of the balloon increases the distal end portion until it contacts the walls of the vascular lumen or other cavity within a patient to form a seal and stabilize the distal end of the catheter. This patent further discloses, and is primarily concerned with, an aiming mechanism for positioning an optical fiber within an arterial lumen so as to direct the fiber towards a particular site therein. Other known devices in this general medical field also include an endobronchial or endotracheal tube having inflatable cuffs which preclude air in the patient's lungs from escaping through the trachea or bronchus.

While the above-cited '653 patent is directed to the aiming or positioning of optical fibers, it does not address the particular problems associated with smoke and debris which are typically encountered in laser surgery. Likewise, the above-mentioned endobronchial and endotracheal tubes address entirely different problems from those which occur in laser surgery.

These aforementioned devices, while providing an effective remedy to various unrelated problems associated with endoscopy, do not teach or suggest any sealing means, or any other means, which solve the specific problem of smoke and debris control encountered in laser surgery.

Accordingly, an object of the present invention is to provide a protective tube for a laser endoscope that prevents the passage of laser smoke towards the oral cavity of a patient and which is adapted to be inserted through the oral cavity and into an esophagus of a patient receiving medical treatment.

Another object of the invention is to provide a protective tube for a laser endoscope that removes debris build-up from the distal end of the endoscope so that this same debris will not adhere to the interior of the protective tube during removal of the endoscope and later cause damage to the endoscope during its reinsertion into the tube.

Another object of the invention is to provide a protective tube for a laser endoscope that is adapted to fit any existing laser endoscope and which may be attached thereto quickly and easily.

Another object of the invention is to provide a protective tube for a laser endoscope that serves as a guide during insertion of the endoscope.

Another object of the invention is to provide a protective tube for a laser endoscope that precludes any tissue injury in the oral cavity and nasal passage.

Another object of the invention is to provide a protective tube for a laser endoscope that may be used for both diagnostic and therapeutic procedures.

Another object of the invention is to provide a protective tube for a laser endoscope that is disposable.

A further object of the invention is to provide a protective tube for a laser endoscope that is easy to manufacture and cost effective to use.

SUMMARY OF THE INVENTION

The present invention, in the preferred embodiment, comprises a structure that accomplishes the foregoing objects by providing a protective tube for a laser endoscope having, on its distal end, a first expandable cuff and a second expandable cuff which is adapted to be inflated by cuff expanding means after insertion of the tube in the esophagus. The first expandable cuff, after expansion, forms a first seal between an outer surface of the tube and an inner surface of the esophagus. The second expandable cuff, after expansion, forms a second seal between an inner surface of the tube and an outer surface of the laser endoscope.

In another embodiment, the second expandable cuff is in the form of an O-ring and includes a plurality of slits that partially radially extend toward the circumference of the O-ring. The O-ring forms a seal in a manner similar to that described in the preferred embodiment.

Specifically, in both embodiments, the first seal should preferably be positioned between the distal end of the outer surface of the protective tube and the upper end of the esophagus so that there is no interference by the tube with the vocal cords and further, so that comfort to the patient is maximized. Moreover, the tube itself must be positioned in the upper part of the esophagus to provide maximum visibility.

Likewise, in the preferred embodiment, it is preferable to position the second seal on the inner surface of the tube between the first seal and the outermost distal edge of the tube such that it contacts the distal end of the outer surface of the endoscope. In the above-mentioned alternate embodiment, it is preferable to mount the O-ring on the end of the tube for increased flexibility. However, the O-ring may be mounted on an inner diameter of the tube, between the first expandable cuff and the end of the tube. This positioning of the second seal, in both embodiments, is preferable so that debris which forms on the distal end of the laser endoscope will be removed therefrom during its removal from the patient as it is pulled through the second seal and out of the protective tube.

The protective tube, in the preferred embodiment, also includes a mouthpiece on its proximal end that precludes damage to the tube from the patient's teeth during the intubation process.

Thus, the inventive device provides a protective tube for a laser endoscope that prevents the passage of laser smoke towards the oral cavity of a patient, removes debris build-up from the distal end of the laser, and is adapted to be inserted through the oral cavity and into the esophagus of a patient receiving medical treatment. The inventive device is inexpensive to manufacture and solves a problem that has not been addressed in the prior art.

The above, as well as other objects and advantages of the invention, will become apparent from the following detailed description of the preferred embodiment, reference being made to the accompanying drawings.

BRIEF DESCRIPTION OF THE DRAWINGS

FIG. 1 is a perspective view of the preferred embodiment of the inventive protective tube, as it appears prior to intubation.

FIG. 2 is a fragmented side view of the distal end of another embodiment of the inventive tube, illustrating one method of mounting the O-ring.

FIG. 2A is another fragmented side view of the tube of FIG. 2, illustrating another method of mounting the O-ring.

FIG. 2B is a plan view, illustrating the O-ring of FIGS. 2 and 2A.

FIG. 5 is an enlarged fragmented perspective view of the distal end of the tube of FIG. 1 and the endoscope of FIG. 3.

FIG. 6 is a fragmented perspective view of the tube of FIG. 1, as it appears during intubation.

FIG. 7 is a cross-sectional view taken along lines 7—7 of FIG. 1 with the endoscope of FIG. 3 during intubation.

FIG. 8 is another cross-sectional view that is similar to FIG. 7 showing a second expanded cuff.

FIG. 9 is a fragmented perspective view of the tube of FIG. 1 and the endoscope of FIG. 3, as they appear during intubation.

DETAILED DESCRIPTION OF THE INVENTION

Figure 3:
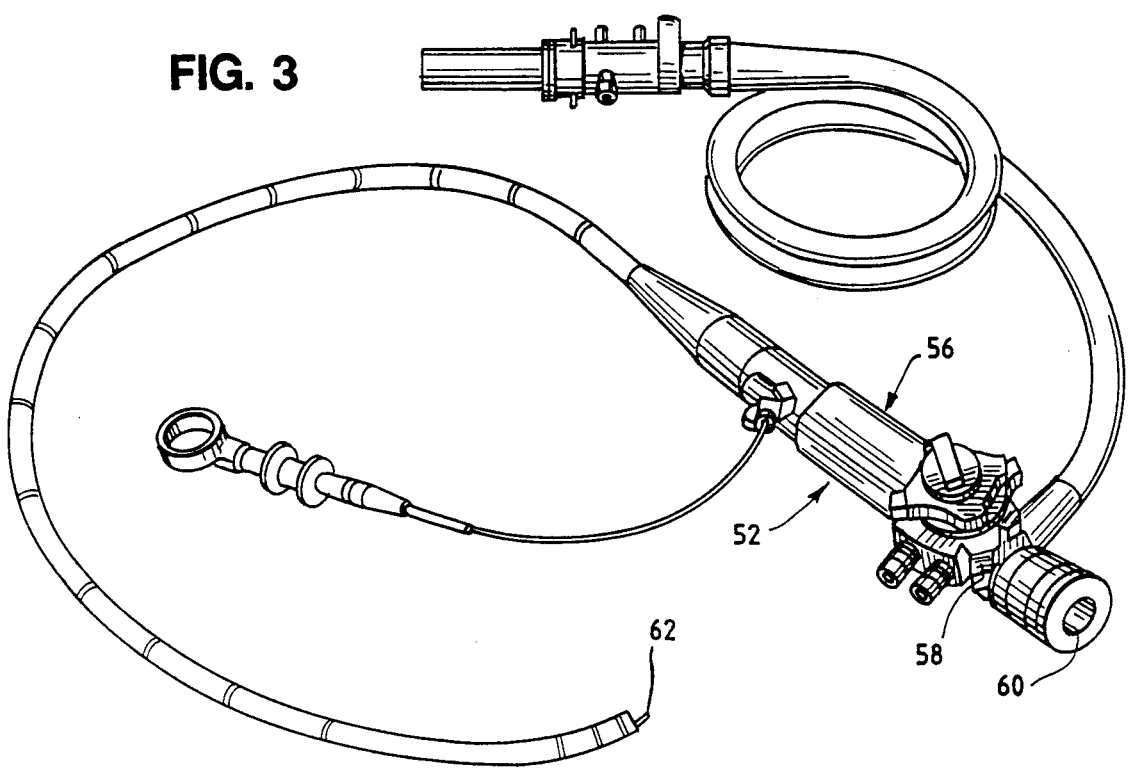
FIG. 3 is a perspective view of an endoscope, such as is adapted to be inserted into the tube of FIG. 1.

Referring first to FIG. 1, the invention provides a protective tube for an endoscopic device generally denoted by the numeral 10 having, in part, a hollow curved resilient member 12 with a mouthpiece 14 attached at its proximal end 16 and a first and second seal means 18 and 20, respectively, attached at its distal end 22. In a first embodiment, first and second sealing means 18 and 20 are inflated by a first and second expanding means 24 and 26, respectively.

Mouthpiece 14 includes a first opening 28 which is adjacent to and coincides with a proximal opening 30 of resilient member 12. Mouthpiece 14 further includes a second opening or slit 32 and hooks 34 which may be used for attaching straps and the like to the protective tube 10. Directly backside of and adjacent to mouthpiece 14 is a short rectangular portion or bite block portion of resilient member 12 (not shown).

A first sealing means 18 is located on the exterior of and near the distal end 22 of resilient member 12. Similarly, a second sealing means 20 is located on the interior of member 12 between the first sealing means 18 and an outer edge 38 of member 12. In the embodiment of FIG. 1, the first and second sealing means 18 and 20 are expandable cuffs which are independently inflated by way of inflation lumens 40 and 42, respectively, which extend along the length of resilient tube 12 and are attached to their respective cuffs. A syringe 44 is used to introduce air into one-way valves 46, 48 of lumens 40, 42, respectively, which causes first and second cuffs 18, 20 to inflate, as shown in FIG. 8.

In another embodiment, shown in FIGS. 2 and 2A, the second sealing means is not an inflatable cuff but is instead an O-ring 50 which is preferably made from soft durometer silicone. Thus, in this embodiment, resilient member 12 does not have two channels which extend along its length but instead has only a single lumen (not shown) for inflating first sealing means 18'.

O-ring 50 is mounted in the inner diameter of tube 10 as shown in FIGS. 2 and 9. However, mounting O-ring 50 on the end of tube 10, as illustrated in FIG. 10, provides increased flexibility.

O-ring 50 may include a plurality of slits 51 which partially radially extend towards the circumference of O-ring 50.

The protective tubes of the embodiments of FIGS. 1 and 2 are adapted to receive an endoscope, such as the endoscope denoted by numeral 52 in FIG. 3. Generally, endoscope 52 includes a proximal end 58 having a device insertion aperture 56, see FIG. 3, and a viewing mechanism 60 which is telescopically mounted therein and a distal end 54 having a viewing lens and light source, as well as an aperture, through which a laser fiber 62 can be passed, and which focuses a laser beam onto a specific area of tissue.

Figure 4:
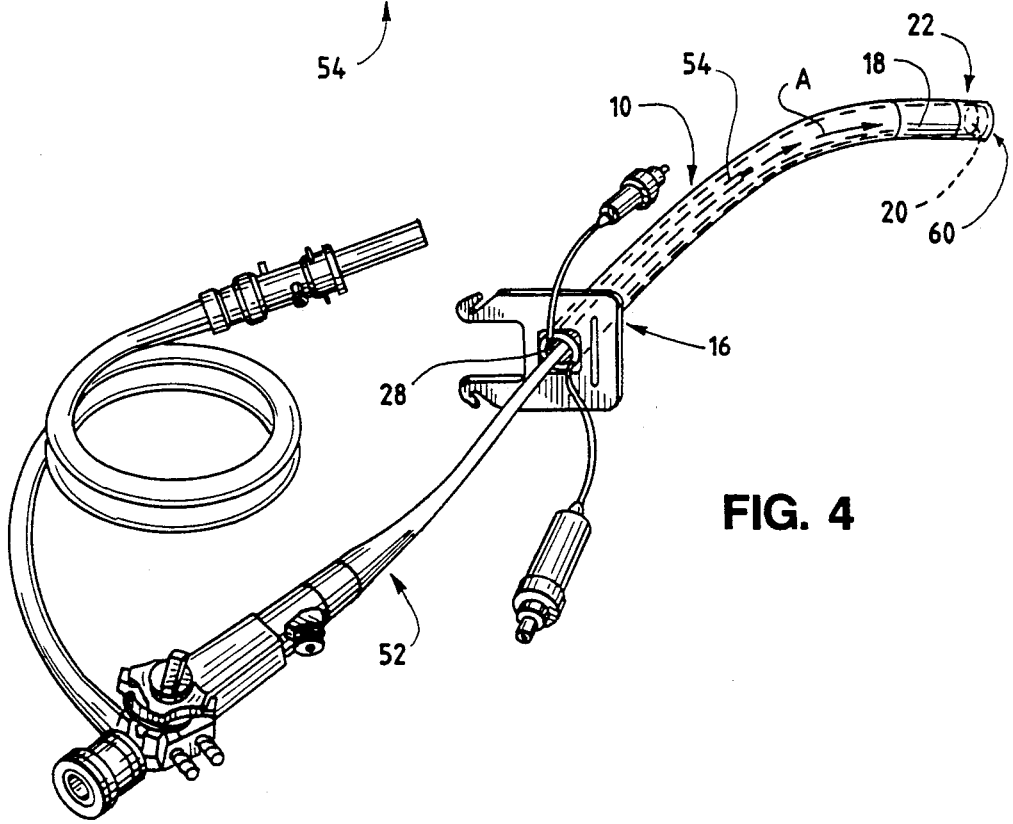
FIG. 4 is a perspective view, illustrating the insertion of the endoscope of FIG. 3 into the tube of FIG. 1.

Referring to FIG. 4, the distal end 54 of endoscope 52 is threaded into the proximal end 16 of tube 10 through first opening 28, and then through tube 12, as indicated by the arrows marked A. Endoscope 52 passes underneath first sealing means 18 and through second sealing means 20 and then exits from the distal end 22 of tube 10 through second opening 64, as shown in FIG. 5. The endoscope 52 may project from second opening 64 of tube 10 at varying distances as needed.

After the insertion of endoscope 52 through tube 10, the patient is intubated with tube 10. Intubation involves inserting tube 10 into a patient's oral cavity, passing it through the cricopharyngeus and positioning and securing it in the upper esophagus.

Referring to FIG. 6, tube 10 is also secured in upper esophagus 66 by inflating first sealing means 18. As previously explained and illustrated in FIG. 1, a syringe 44 is used to introduce air into one-way valve 46 of lumen 40 which causes first sealing means 18 to expand outwardly, as indicated by the arrows B in FIG. 7. Alternatively, lumen 40 may be inflated with saline solution. First sealing means 18 is expanded until contact is made with the upper inner wall 68 of esophagus 66.

FIG. 7 illustrates the appearance of laser 52 after it has been threaded through tube 10 and before second sealing means 20 have been inflated.

Second sealing means 20 are inflated in the same manner as the first sealing means. Syringe 44 is used to introduce air into one-way valve 48 of lumen 42 which causes second sealing means 20 to inflate (see FIG. 1). Lumen 42 may also be inflated with saline solution. Second sealing means 20 expand inwardly, as shown in FIG. 8 by the arrows marked C, until contact is made with an outer distal surface of laser endoscope 52.

First sealing means 18 and second sealing means 20 are maintained in an inflated state, as shown in FIG. 9, until the laser process has been completed. The inflated first and second sealing means 18 and 20, respectively, preclude the smoke produced during the operation of the laser from travelling through esophagus 66 and entering a patient's nasal passage and oral cavity. During the laser procedure, endoscope 52 may be gently manipulated out of tube 10. During the removal process of endoscope 52, second sealing means 20 is maintained in an inflated state so that any debris on the distal end 22 of endoscope 52 will be scraped off as endoscope 52 is pulled through second sealing means 20. The removal of debris from the endoscope is essential to optimal operation of the instrument as the debris may initially adhere to the interior of tube 10 during the removal process of the endoscope 52 and subsequently adhere to the endoscope itself during reinsertion into tube 10.

The protective tube 10 has not been described in terms of approximate measurements, as it should be understood that the size of the tube 10 may vary according to the dimensions of the endoscope to be protected and the age and physiology of the patient.

Therefore, it should be recognized that, while the invention has been described in relation to a preferred embodiment thereof, those skilled in the art may develop a wide variation of structural details without departing from the principles of the invention. Accordingly, the appended claims are to be construed to cover all equivalents falling within the true scope and spirit of the invention.

The invention claimed is:

1. A protective tube for a laser endoscope that prevents the passage of laser smoke towards the oral cavity of a patient, removes debris from said endoscope and which is adapted to be inserted through the oral cavity and into an esophagus of a patient receiving medical treatment, said protective tube comprising a resilient member having a proximal end and a distal end, said proximal end including a mouthpiece, the improvement comprising: said distal end including a first expandable cuff and a second expandable cuff which are adapted to be inflated by cuff expanding means after insertion of said tube in said esophagus, said first expandable cuff after expansion being capable of forming a first seal between an outer surface of said tube and an inner surface of said esophagus and said second expandable cuff after expansion being capable of forming a second seal between an inner surface of said tube and an outer surface of said laser endoscope.

2. A protective tube for a laser endoscope that prevents the passage of laser smoke towards the oral cavity of a patient, removes debris from said endoscope and is adapted to be inserted through the oral cavity and into an esophagus of a patient receiving medical treatment, said protective tube comprising a curved resilient member having a proximal end and a distal end, said proximal end including a mouthpiece and said distal end including a first expandable cuff and a second expandable cuff which are adapted to be inflated by cuff expanding means after insertion of said tube in said esophagus, said first expandable cuff after expansion being capable of forming a first seal between an outer surface of said tube and an inner surface of said esophagus and said second expandable cuff after expansion being capable of forming a second seal between an inner surface of said tube and an outer surface of said laser endoscope.

3. The protective tube of claim 2 wherein said outer surface of said tube is on said distal end of said tube.

4. The protective tube of claim 2 wherein said inner surface of said tube is on said distal end of said tube between said first expandable cuff and an outermost distal edge of said tube.

5. The protective tube of claim 2 wherein said outer surface of said laser endoscope is on a distal end of the endoscope.

6. A protective tube for a laser endoscope that prevents the passage of laser smoke towards the oral cavity of a patient, removes debris from said endoscope and which is adapted to be inserted through the oral cavity and into an esophagus of a patient receiving medical treatment, said protective tube comprising a resilient member having a proximal end and a distal end, said proximal end including a mouthpiece and said distal end including a first sealing means and a second sealing means, said first sealing means forming a first seal between an outer surface of said tube and an inner surface of said esophagus and said second sealing means forming a second seal between an inner surface of said tube and an outer surface of said endoscopic laser, said second sealing means being an O-ring and including a plurality of slits which partially radially extend toward the circumference of said O-ring.

* * * * *